(12) United States Patent
Chi et al.

(10) Patent No.: US 7,989,195 B2
(45) Date of Patent: Aug. 2, 2011

(54) HETEROTROPHIC ALGAL HIGH CELL DENSITY PRODUCTION METHOD AND SYSTEM

(75) Inventors: Zhanyou Chi, Pullman, WA (US);
Zhiyou Wen, Blacksburg, VA (US);
Craig Frear, Pullmann, WA (US);
Shulin Chen, Pullmann, WA (US)

(73) Assignee: Washington State University Research Foundation, Pullman, WA (US)

( * ) Notice: Subject to any disclaimer, the term of this patent is extended or adjusted under 35 U.S.C. 154(b) by 66 days.

(21) Appl. No.: 12/132,131

(22) Filed: Jun. 3, 2008

(65) Prior Publication Data
US 2009/0209014 A1 Aug. 20, 2009

Related U.S. Application Data

(60) Provisional application No. 61/029,974, filed on Feb. 20, 2008, provisional application No. 61/029,969, filed on Feb. 20, 2008.

(51) Int. Cl.
*C11C 1/00* (2006.01)
*C12N 1/12* (2006.01)
*A01N 37/00* (2006.01)
*A61K 31/20* (2006.01)

(52) U.S. Cl. ........ 435/271; 435/257.1; 514/558

(58) Field of Classification Search ........ 435/257.1, 435/271; 514/558
See application file for complete search history.

(56) References Cited

U.S. PATENT DOCUMENTS

| 5,130,242 | A * | 7/1992 | Barclay ......... 435/134 |
| 6,607,900 | B2 * | 8/2003 | Bailey et al. ......... 435/134 |
| 2007/0238905 | A1 * | 10/2007 | Arrendondo et al. | |

OTHER PUBLICATIONS

Yokochi et al., 1998, Applied Microbiology and Biotechnology, vol. 49, p. 72-76.*
Wu et al., 2005, Process Biochemistry, vol. 40, p. 3103-3108.*
Pyle, D.J., "Producing Docosahexaenoic Acid (DHA)-Rich Algae from Biodiesel-Derived Crude Glycerol: Effects of Impurities on DHA Production and Algal Biomass Composition." Journal of Agricultural and Food Chemistry. 2008, 56, pp. 3933-3939.

* cited by examiner

*Primary Examiner* — Shin-Lin Chen
(74) *Attorney, Agent, or Firm* — Whitham Curtis Christofferson & Cook, PC

(57) ABSTRACT

A multiphase culturing process for high density heterotrophic microalgal growth uses crude glycerol as the primary carbon source and produces ω-3 fatty acids. The process uses multiphase growth conditions that decouple the phases of increasing cell density and increasing cell size and fatty acid production. The entire process is integrated with biodiesel production.

13 Claims, 4 Drawing Sheets

HETEROTROPHIC ALGAL HIGH CELL DENSITY PRODUCTION METHOD AND SYSTEM

CROSS REFERENCE TO RELATED APPLICATIONS

This application claims benefit of U.S. provisional patent applications 61/029,974 filed Feb. 20, 2008, and to 61/029,969 filed Feb. 20, 2008, the complete contents of both of which are hereby incorporated by reference.

BACKGROUND OF THE INVENTION

1. Field of the Invention

The invention generally relates to methods of producing ω-3 fatty acids using microalgae. In particular, the invention provides a multiphase method for high density heterotrophic microalgal growth and production of ω-3 fatty acids. The multiphase method decouples cell division, cell growth, and ω-3 fatty acid production by controlling optimal conditions for each in separate reactors. The decoupling and optimization result in overall improvements in algal, lipid, and polyunsaturated fatty acid (PUFA) yield and productivity. In addition, the process has been integrated to a biodiesel refinery by utilizing waste feedstocks such as crude glycerol, a byproduct of biofuel generation, as the primary carbon source. Use of in situ transesterification and fractional distillation processes allow for products from the algal growth process to include not only PUFA lipids generated by the microalgae, but also non-PUFA lipids which can be used in biofuel generation, thereby forming an integrated microalgae-biofuel system for sale of biodiesel methyl esters and PUFA in a distinguishing methyl ester form.

2. Background of the Invention

Recent sociopolitical and economic developments have highlighted the need for efficient and scalable methods for bioproduct generation and utilization. While much energy has focused on the utilization of existing agricultural products, such approaches have non-desirable secondary effects. Specifically, the diversion of productive cropland from food production to the production of useful chemicals and materials ultimately results in an increase in product costs. This has led to enhanced interest in the development of methods for the generation of valuable products from marginal land and/or from waste streams or low value materials (Gonzalez-Pajuelo, 2006; Papanikolaou, 2002; Narayan, 2005; Meesters, 1996). For example, crude glycerol (glycerol is also referred to as "glycerin") is a byproduct of the transesterification reaction that is used to make biodiesel from plant sources. Due to recent increases in biofuel production, the world market is currently experiencing an enormous glut of crude glycerol. Various uses of crude glycerol have been proposed. Purification can be carried out to produce purified glycerol; crude glycerol can be used in animal feed (especially for pigs); and crude glycerol may be used as a substrate for fermentation by anaerobic bacteria (e.g. *Clostridium* sp.) to produce useful products such as lactic acid, propionic acid, etc., as well as active programs to convert waste glycerol to antifreeze, bioploymer precursors and soaps. However, excess crude glycerol is still being produced and is generally disposed of by simply burning it, a wasteful process. A need exists to develop additional methods for dealing constructively with "waste" crude glycerol.

Another example is the renewed interest in the harvesting of products derived from algae, particularly from heterotrophic microalgae with known capabilities for generating and storing within their biomass large quantities of lipids, and in particular omega-3 lipids with known health benefits. Omega-3 polyunsaturated fatty acids (ω-3 PUFAs) are a group of fatty acids containing two or more double bonds, of which the last double bond is located at the third carbon atom from the methyl terminal. For a long time, the beneficial effects of ω-3 PUFAs have been recognized by epidemiological surveys that revealed that Eskimos, who consume large amounts of deep-sea fish, rarely suffered from heart diseases. Docosahexaenoic acid (DHA, 22:6), with a 22 carbon chain and 6 double bonds, is one of the more important (ω-3 PUFAs and is known to have particular beneficial effects in fetal and infant brain and ocular development. The inclusion of supplementary DHA in infant formulas is strongly recommended by the World Health Organization (WHO) (FAO/WHO Expert Committee, 1994). Also, research continues to demonstrate the need for DHA beyond infancy, with studies suggesting a positive correlation between DHA consumption and the reduced risk of age-related neurological disorders, such as Alzheimer's and dementia (Ward and Singh, 2005). As a result, DHA is not only used as an additive in infant formulas, but also in adult dietary food and beverages. Examples include cheeses, yogurts, spreads and dressings, and breakfast cereals. Notably, these markets may have much greater growth potential than infant formulae, thereby substantially elevating the entire DHA market potential (Ward and Singh, 2005).

The conventional source of ω-3 PUFAs is predominantly fish oil and seal oil. Cod, salmon, sardine, mackerel, menhaden, anchovy, and tuna are generally used for fish oil production. The quality of fish oil depends on the fish species, the season and the geographical location of catching sites. As marine fish oil is a complex mixture of fatty acids with varying chain lengths and degrees of unsaturation, DHA must be refined from fish oil for use in nutraceutical/pharmaceutical applications. The purification of DHA from low-grade fish oil is difficult and costly (Belarbi et al., 2000). In addition, marine fish stocks are subjected to seasonal and climatic variations, and may not meet the requirement for providing a steady supply for the increasing demands of DHA.

It is known that fish, like humans, are not capable of synthesizing PUFA de novo. Much of their PUFA is derived from the primary producer in the oceanic environment: microalgae or algae-like microorganisms. There are a large number of microalgae in nature which produce PUFAs in general and DHA in particular, but only a few species have demonstrated production potential on an industrial scale. This is mainly due to the low specific growth rates and low cell density of the algae, since in many cases they can only grow under photoautotrophic conditions.

Intensive research into the production capabilities of these microalgae led researchers and commercial industries to focus on and develop heterotrophic algal production processes for DHA. As of late, the two algae used commercially and showing the greatest commercial promise are the heterotrophic dinoflagellate *Crythecodinium cohnii* and strains of traustochytrid marine protists. Developments of commercial processes for production of DHA with these two algae has benefited from the fact that they can accumulate high oil contents in their biomass (10-50%, w/w) and produce a high percentage of total lipids as DHA (30-70%). High biomass densities (up to 109 g/L) and DHA concentrations of 20 g/L have been achieved in carbon fed batch cultures of the marine species, *C. cohnii*, although prolonged culture times (400 h) were required. Studies have demonstrated that DHA productivities of 1-1.5 g/(L day) are achievable with this strain (Ward and Singh, 2005).

However, the best microbial sources of DHA are *Thraustochytrids*, specifically the genera *Thraustochytrium* and *Schizochytrium*. *Thraustochytrium* and *Schizochytrium* are unicellular algal or algal-like protists, members of the order Thraustochytriales; family Thraustochytriaceae; genus *Thraustochytrium* or *Schizochytrium*. *Schizochytrium* replicates by both successive bipartition and by release of zoospores from sporangia, whereas *Thraustochytrium* strains only replicate by formation of sporangia/zoospores. Studies with thraustochytrids have established these marine protists as preeminent industrial strains for the production of DHA. Initial research at relatively low cell densities (5-20 g/L) established the capacities of *Thraustochytrium* species to accumulate greater than 50% of their lipids as DHA and to produce >1 g DHA/L of culture, with productivities of about 0.2 g/(L day) (Ward and Singh, 2005). *Schizochytrium* species with even higher growth rates have been isolated. Under glucose and nitrogen-fed batch conditions, with incorporation of sodium sulfate as a main sodium source and with control of glucose concentrations, pH and oxygen levels, selected strains have been shown to grow to high biomass densities (100 g/L) in short fermentation cycles (90-100 h), accumulating 4045 g/L of DHA and DHA productivities of >10 g/(L day). These excellent performances have made *Schizochytrium* the producer of choice in the DHA industry (Bailey et al., 2003).

Specific industrial utilization and commercial culture conditions of the genera *Thraustochytrium* or *Schizochytrium* for the generation of PUFA products is discussed in detail in U.S. Pat. No. 5,130,242 (Barclay, which is incorporated herein by reference). In '242 and related filings, U.S. Pat. Nos. 5,340,742 and 6,977,167, (both to Barclay, the complete contents of both of which are hereby incorporated by reference) algae from these genera are cultured in closed reactors under controlled salt, oxygen, and temperature, and carbon and nitrogen source concentrations which were tailored to maximize the production of the PUFA product. However, the carbon and nitrogen sources were derived solely from relatively high-value agricultural products, i.e. the use of crude glycerol is not discussed.

Within these disclosures much focus has been directed toward the increase in biomass and PUFA product yield. In U.S. Pat. Nos. 5,130,242 and 6,977,167 it was disclosed that, through the maintenance of a relatively high concentration of phosphate, a sustained growth can be maintained, which enables, in part, the production of a high density culture. Moreover, through the specific control of the nitrogen source, or when the nitrogen source becomes limited (either through controlled addition or static initial supply) for some time period prior to cell harvesting the biomass will have an increased concentration of PUFA. Similarly, in U.S. Pat. No. 6,607,900 (Bailey et al., the complete contents of which are hereby incorporated by reference) a two phase fed-batch fermentation process, wherein a first phase aimed at biomass density is followed by a second lipid production phase, is disclosed. As described in '900, and similar to the process disclosed in U.S. Pat. Nos. 5,130,242 and 6,977,167, the biomass density phase comprises a fermentation medium containing sugar and amino acid derivatives (as a nitrogen source) and the lipid accumulation phase comprises mostly sugar with limited amino acid derivatives within the fermentation medium, with the added caveat that the oxygen concentration during the lipid accumulation phase is less than the oxygen concentration during the biomass accumulation phase.

While relatively little attention has been directed toward the specific functional relationships between the nutrient variables and the cell state, some information is available. In U.S. Pat. No. 5,340,742, growth methods are described wherein non-chloride salts, specifically sodium sulfate and/or low chloride concentrations, were utilized to provide 1) decreased corrosion of the fermentation and cell harvesting hardware and 2) a smaller aggregate cell size while maintaining a high PUFA concentration. Using the process described in U.S. Pat. No. 6,607,900, with the fed-batch mode, at least 100 g/L of biomass density can be obtained by feeding the carbon source and the nitrogen source at a sufficient rate. In this process, the fermentation condition comprises a biomass density increasing stage and a lipid production stage. Both the carbon source and the nitrogen source are added in the biomass density increasing stage, while only a carbon source is added during the lipid production stage. The level of dissolved oxygen in the medium during the fermentation biomass density increasing stage is at least about 4%, and during the lipid production stage is less than about 3%. The preferred temperature in this process is about 30° C. The lipid production rate of this process can reach 1.0 g/L/hr, and the DHA in the lipids is about 40%. On the whole, according to U.S. Pat. No. 6,607,900, the DHA production rate can reach 0.5 g/L/hr.

In summary, U.S. Pat. No. 6,607,900 teaches culturing microalgae (e.g. Thraustochtriales of the genera *Thraustochytrium* and *Schizochytrium*) in two stages. The first is a biomass density increasing stage during which the dissolved oxygen is at least about 8% and preferably about 4%. In contrast, in the second "production" stage, during which the primary activity of the algae is not increasing biomass but producing lipids, the amount of oxygen is decreased to about 1% or preferably 0%. U.S. Pat. No. 6,607,900 teaches using temperatures of at least 20° C., more preferably 25° C., and most preferably 30° C., without specifying which temperatures are suitable for which stage. However, U.S. Pat. No. 6,607,900 states that, because cold water can retain a higher amount of dissolved oxygen than warm water, a "higher fermentation medium temperature has the additional benefit of reducing the amount of dissolved oxygen . . . ". Thus, U.S. Pat. No. 6,607,900 suggests that higher temperatures are advantageous during the production stage when low or no oxygen is preferred. U.S. Pat. No. 6,607,900 also teaches a total fermentation time of from about 90 to about 100 hours. In addition, U.S. Pat. No. 6,607,900 teaches that the carbon source for the process is preferably nonalcoholic, and preferably a carbohydrate such as corn syrup. These teachings would suggest ruling out the use of crude glycerol (glycerol is an alcohol).

In addition, U.S. Pat. No. 5,130,242 discusses a two-stage algae fermentation process to produce lipids. The first stage is an exponential growth stage, and the second is a stationary lipid production stage. During the latter, nitrogen limitation stimulates lipid production. However, U.S. Pat. No. 5,130,242 teaches that the nitrogen-limited period should be relatively short, e.g. 6-24 hours. According to U.S. Pat. No. 5,130,242, the preferred nutritive sources for both carbon and nitrogen are grains and certain hydrolyzed waste products such as stillage, a waste product in corn to alcohol fermentations. However, the use of crude glycerol is not discussed. "Crude glycerol" differs from "glycerol" in that, as a byproduct of the biodiesel production process, crude glyderol contains roughly 70-80% glycerol mixed with industrial process contaminants such as free fatty acid anions, mono and diglycerides, alcohol and salts. These substances come from the raw material or from incomplete reactions during the fuel production process.

Further, U.S. Pat. No. 6,582,941 (Yokochi et al.) discloses *Schizochytrium* genus strain SR21 as capable of producing highly unsaturated fatty acids. Glycerol is one suggested carbon source. However, the use of byproducts such a crude glycerol is not discussed. (See also Yokochi et al., 1998.)

Finally, International patent application WO 2004/083442 (Kumar et al.) describes a method of increasing the levels of PUFAs in cultured thraustochytrids by storing them in the cold after 2-5 days of growth. Crude glycerol is not suggested as a carbon source.

SUMMARY OF THE INVENTION

The present invention provides an improved and efficient high cell density culture method for the production of ω-3 PUFAs, particularly DHA. The method takes advantage of the unique biology of the microflora that produces DHA by mimicking the decoupling of cell division and cell growth/size increase through accumulation of lipids. This decoupling via control of operating parameters in separated dedicated reactors allows for an enhanced cellular population or density which can then later be grown to maximal limits for accumulation of lipids and PUFA, especially DHA. The result is a process with higher potential for yields and productivity. In addition, the method provides a solution to the glut of crude glycerol in that the primary carbon source used in the method is crude glycerol. The use of crude glycerol not only helps to decrease the excess quantity of this substance but also decreases the cost of algal fermentation since it becomes unnecessary to use more purified, and thus most costly, feedstocks. In addition, some of the lipids produced by the microalgae, e.g. those that are not ω-3 rich, can be isolated and used as components of biofuel (also referred to as biodiesel herein), which will in turn generate more crude glycerol for use as a feedstock. Lastly, the isolation of separate (ω-3 rich and non-ω-3 rich lipids is accomplished via an in situ trans esterification and subsequent fractional distillation process that can be accomplished without need for oil extraction or separation from an aqueous environment, resulting in two methyl ester products; an ω-3 rich methyl ester nutraceutical and a non-ω-3 rich methyl ester for use as biodiesel fuel. Thus, in one embodiment of the invention, the manufacture of biofuel and the production of ω-3 PUFAs are fully integrated.

As disclosed herein, the process of PUFA production by microalgae comprises three distinct phases: (1) a cell proliferation phase tailored to increase the overall cell count; followed by (2) a biomass and lipid accumulation phase tailored to increase the volume of existing cells, and in particular the volume of lipids; which is then followed by (3) a shorter "polishing" step whereby the lipid concentration is further intensified and the lipid profile is adjusted towards greater PUFA and primarily DHA production. Variables, such as carbon and nutrient feed types and concentrations, dissolved oxygen content, and temperature, are shifted during the three-stage algal growth process to ultimately induce maximum biomass, lipid and DHA production.

In particular embodiments, the three-stage process may be carried out within a single vessel, wherein the growth conditions are modulated at the appropriate time. Further embodiments comprise process segmentation wherein the three distinct growth phases occur in physical isolation using combinations of continuous and fed-batch processes, i.e. the process is carried out using two or more dedicated reactors run in series so that each stage of the process can be individually optimized. In some embodiments, the micro-algae used in the fermentation process derive from the genus *Schizochytrium* with a specific example as provided herein utilizing the species *Schizochytrium limacinum* SR 21. Obtaining a large amount of cells is crucial for lipid production, since the maximum body weight of each single cell is limited, and each cell can only hold a certain amount of lipid inside the cell. More cells per unit volume of broth results in more cell biomass and greater quantities of lipids in the end. The present invention provides a method for first shunting the majority of cellular activity towards cell division and production of a large number of cells quickly, as opposed to utilizing cellular activity to simultaneously divide and grow. The result is a high cell density which can, in later stages, be fed nutrients to attain maximal cell and lipid size, resulting in overall increases in biomass and lipid yield.

Significantly, the entire process can be efficiently integrated within the biodiesel refinery process. This is because the main feedstock utilized by the micro-algae and for which the whole process and choice of particular organism is designed is crude glycerol, which is produced as a by-product of the biodiesel refining process, rather than sugar or other non-alcoholic carbohydrates. After some pre-treatment which can be performed on-site, the crude glycerol is used as the carbon source to ferment the algae. The algae that are produced can then be put through a downstream in situ trans-esterification and fractional distillation separation process whereby the algae biomass is treated to produce: (1) ω-3 rich methyl esters for food/nutraceutical sale; and (2) non-ω-3 rich methyl esters for use in the production of biofuel. During subsequent biofuel production, crude glycerol is again reclaimed as carbon feed for future fermentation and algae production. Finally, algal biomass waste can be used as an animal feed both internally in the fermentation process or externally, e.g. in animal feed.

DETAILED DESCRIPTION OF THE PREFERRED EMBODIMENTS OF THE INVENTION

Figure 1:
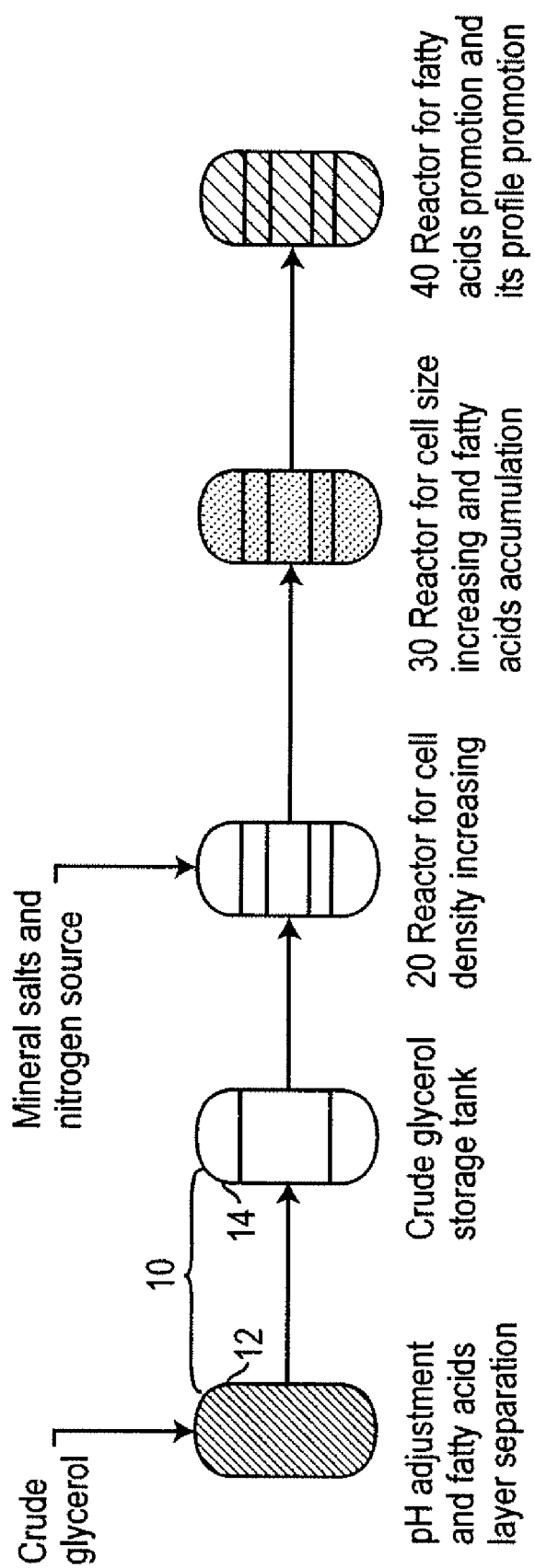
FIG. 1. Schematic representation of an apparatus for multiphase fermentation.

The present invention is based on the development of improved methods for the generation of omega-3-rich PUFAs from microalgae. In studies of the marine algae *Schizochytrium*, it has been discovered that, in nature, the metabolic status of reproduction and lipid accumulation is decoupled. The growth of this algae can be divided into two distinct stages: (1) a cell number increasing or reproduction stage during which cell proliferation rapidly increases cell number with little increase in the size and weight of each cell; and (2) a cell size increasing stage during which the cells decrease or cease proliferation and instead become enlarged due to the accumulation of fatty acids. Notably, the optimal culture conditions for the two stages are different and are not linearly related, as can be seen in the data presented in Table 1, which was obtained under the following conditions: *Schizochytrium limacinum* SR 21 was cultured in medium consisting of 100 g/L glycerol, 5 g/L corn steep solids, 1 g/L ammonium acetate, and with all the mineral salts present in sea water. The culture was kept at 25° C. in shaker flasks with a 175 rpm orbital speed for 7 days. The results are shown in Table 1. The inoculation cell density was about 2 million cells/ml. For the first 48 hours, the cell density increased rapidly and reached 42.5 million cells/ml. After that, the cell density increased very slowly, finally increasing to 58.5 million cells/ml. In contrast, the biomass concentration, i.e. dry cell weight, increased slowly during the first 48 hours, resulting in only 6.9 g/L of biomass at 48 hours. After this, the dry cell weight kept increasing and the final dry cell weight was 24.6 g/L. Calculation of the "cell body weight" of each cell, by dividing the cell biomass concentration by cell density, showed that the cell body weight at 48 hours was 0.161 ng/cell, whereas the final cell body weight was 0.420 ng/cell, indicating that cell size was more than doubled.

TABLE 1

Relationship between cell number, cell dry weight and cell body weight vs time in culture

| | Culture time (days) | | | | |
|---|---|---|---|---|---|
| | 1 | 2 | 3 | 5 | 7 |
| Cell number ($10^6$ cells/ml) | 25.2 ± 1.9 | 42.5 ± 4.2 | 47.4 ± 11.9 | 64.0 ± 7.8 | 58.5 ± 7.7 |
| Dry cell weight (g/L) | 3.5 ± 0.1 | 6.9 ± 0.2 | 10.1 ± 0.6 | 16.4 ± 0.8 | 24.6 ± 1.6 |
| Cell body weight (ng/cell) | 0.137 | 0.161 | 0.214 | 0.256 | 0.420 |

Note that in this non-optimized single flask culture, the cell number increases extensively in the first day and then plateaus (or even decreases, e.g. between days 5 and 7) while the cell body weight increases significantly only later in the fermentation (e.g. after day 3, and especially between days 5 and 7). By controlling the fermentation parameters more tightly in a bioreactor, conditions based on this non-linear relationship have been developed to allow for almost exclusive cell division during the first day(s), to be then followed by an almost exclusive cell growth stage, resulting in overall increases in biomass and lipid yield and productivity. Based on this discovery, separate culture conditions to optimize the two stages have been developed, and by using a strategy of "shifting" between these phases, significant increases in cell culture density and lipid accumulation and profile have been produced. Inclusion of a third polishing step is also carried out whereby conditions are controlled to both maximize lipid production and generate a preferred lipid profile enriched in PUFA and in particular, DHA.

The metabolic flux in the reproduction stage is strong, since biosynthesis of nucleic acids, protein, enzymes, and other materials in the cell requires large amounts of nitrogen and amino acids. Oxygen is consumed rapidly to oxidize the carbon source to provide both low molecular weight carbon and energy for cell reproduction. In addition, during proliferation, a higher culture temperature is preferred to maintain optimal enzyme activity. Conversely, during the lipid accumulation, a low temperature along with low consumption of oxygen is preferred. Enzyme biosynthesis requires some nitrogen, but lipid accumulation is a process of converting a carbon source to long chain fatty acids, and requires little nitrogen. Optimal conditions for cell reproduction and lipid accumulation are thus different.

The present invention thus provides a two-stage, integrated, high-cell density fermentation process for production of omega-3-rich microalgae which primarily focuses on the important step of decoupling the cell number and cell growth steps, and which is followed by a third, polishing step to obtain a preferred lipid profile. The methods of the invention can be carried out in a single fermentor by manipulating growth conditions within the fermentor. However, in a preferred embodiment, the three-stage process uses separate reactors and takes advantage of the algae's unique growth processes by individually controlling operating conditions in each fermentor. A three-stage fermentation apparatus suitable for this process is illustrated in FIG. 1, where 10 represents a crude glycerol feedstock source. Feedstock source 10 may include a tank 12 for pH adjustments and fatty acid layer separation, and a crude glycerol storage tank 14. Tanks 12 and 14 may be combined into a single tank. The first stage, carried out in a first reactor 20, is focused on increasing cell number, and culture conditions are adjusted accordingly. The second stage, carried out in a second reactor 30, is focused on cell mass and fatty acid accumulation, and is carried out under conditions that favor those attributes. Operating conditions in a third reactor, 40, induce a third stage during which the fatty acid profile is further modified to include an even higher percentage of DHA and/or omega-3 fatty acids. Alternatively, culture conditions within second reactor 30 may be adjusted from second stage growth conditions to third stage growth conditions without transferring the cells to a different reactor. Those of skill in the art are familiar with suitable types of fermentors (reactors) for use in the invention, as well as with the elements that are necessary for connecting them to carry out either fed-batch or continuous culture, to monitor internal reactor conditions, to agitate cells, to add or remove cells, etc.

Operating conditions that are controlled and shifted to induce maximum production in the two stages include carbon and nutrient feed types and concentrations, dissolved oxygen content, and temperature. In the first fermentor, the culture conditions are controlled as follows: high temperature, i.e. 28-33° C.; low carbon source concentration, 10-40 g/L; high nitrogen concentration, 1.0-1.5 g/L; and high dissolved oxygen concentration, 20%-50%. The operation mode in this fermentor can be fed-batch or continuous culture. After approximately 24 hours, the cell density in the first fermentor reaches about 400 million cells/ml, preferably about 600 million cells/ml, and most preferably about 1,000 million cells/ml.

At the end of the first stage of fermentation, the cells are transferred to the second fermentor one time (fed-batch mode), or continuously (continuous culture mode). In the second fermentor, the cells grow to a larger size and accumulate lipids. The operation of the second fermentor can also be either fed-batch or continuous. In the second fermentor, if the culture mode is fed-batch, at first, the temperature is controlled at 30° C.; dissolved oxygen (DO) is controlled at 3%-5%; carbon source concentration is at 30-50 g/L; and the nitrogen concentration is kept at 0.5-1.0 g/L. When the speed of increase of biomass concentration slows (e.g. when the cells leave "log" or exponential growth phase and enter a stationary phase, where cell numbers are relatively constant, as evidenced through on-line monitoring of the fermentation process), it has been noted that the DHA content in the biomass is about 13-17%. The DHA content can then be further increased in a third "polishing" stage. This third stage may take place in a separate fermentor, or may be induced or initiated in the same fermentor by further decreasing the temperature in the fermentor to 20-25° C., decreasing the DO to 0%-0.5%, and completely stopping the addition of nitrogen. At the end of the entire process, which takes approximately 5 days, the nitrogen is depleted, and the DHA content is about 20-22% of the dry biomass. Alternatively, if the culture mode is continuous, the temperature in the second fermentor is controlled at 25-30° C.; DO is controlled at 1%-3%; carbon source concentration is at 30-50 g/L; and the nitrogen concentration is kept at 0.1-0.5 g/L by feeding. The time of incubation in the second fermentor under these conditions is approximately 3-4 days. Under these conditions of continues feed, the DHA content in the biomass is typically about 17-20% at the end of the culture period.

The result of the three-stage process is typically a five-day fermentation regime that allows for final high cell densities (~150 g/L) and final high productivity (~1.2 g/L hr) of algae with total fat, PUFA and DHA yields of ~50, 25 and 20%, respectively. Those of skill in the art will recognize that these values may vary somewhat in the practice of the invention. For example, total fat production will generally be in the range of from about 40% to about 60% of dry biomass, and preferably from about 55% to about 65%. Likewise, the yield of PUFAs will be in the range of from about 12% to about 26% of dry biomass, and preferably from about 20% to about 30%. Similarly, for DHA, the range of yield will be from about 16% to about 22% of dry biomass, and preferably from about 20% to about 25%. The productivity of dry biomass is in the range of from about 1 g/L/hr to about 2 g/L/hr, and preferably from about 1.8 g/L/hr to about 3.0 g/L/hr while the productivity of DHA is in the range of from about 0.3 g/L/hr to about 0.45 g/L/hr, and preferably from about 0.4 g/L/hr to about 0.5 g/L/hr.

In regard to the innovative use of crude glycerol, successful application of the proposed process could have a significant impact on the biodiesel industry as it helps to solve the problem of waste glycerol treatment in the biodiesel industry. A crude glycerol source 10 is integrated into the three-stage system, as illustrated in FIG. 1. Waste or crude glycerol produced during biofuel production will be a threat to the environment if it cannot be properly treated and additionally will be an added burden to burgeoning biodiesel industries because of its negative value. Present open market prices for crude glycerol are 5 cents/pound and conceivably could drop even further as production ramps up (commodity market quotes). Converting this waste glycerol into value-added bioproducts is definitely a better choice for treatment of this glycerol. Since utilization of the biodiesel waste leads to increased economic viability of the biodiesel industry as well as reduction in the potential impact to the environment for the disposal of this waste stream, the present invention is beneficial not only to biotechnology but also to industry, security, and energy enhancement.

A considerable portion of the fats contained within the algae biomass are not omega-3 and as such are quite suitable and useful, for example, as fat/oil components in a biodiesel production process. Therefore, in another aspect of the invention, the production of lipids by algae both 1) uses a byproduct of biodiesel production and 2) produces biodiesel components, as well as the PUFA and/or DHA nutraceutical, in an integrated biodiesel refinery. Any suitable method for fat extraction (e.g. solvent extraction) and transesterification (e.g. standard drying and treatment with alcohol and base) can be used to convert the fats within the biomass to methyl esters. This methyl ester mixture can subsequently be fractionated using distillation processes already present within the refinery but modified for this purpose to make both ω-3 rich methyl esters for sale as food/nutraceuticals and non-ω-3 rich methyl esters for sale as biodiesel. Notably, this PUFA methyl ester is distinguishable from other algal PUFA products in that its chemical form is a methyl ester rather than a fatty acid. By completing down-stream separation of the fats and/or fatty esters from the algal biomass and subsequently fractionally separating the different fatty acids or fatty esters, the biodiesel-suitable fatty acids can then be re-inserted into the biodiesel system while the omega-3 fatty acids are retained and marketed. Thus, a truly integrated biodiesel-algae process is developed whereby not only is the crude glycerol by-product utilized but it is utilized for additional biodiesel (and crude glycerol) production together with the new omega-3 fatty acid product. The DHA heterotrophic algae producer will benefit from this invention, since using crude glycerol as the carbon source will significantly reduce the cost of the algae culture process (see Example 3 for a cost analysis). Currently, although heterotrophic algae culture is taking on a more and more important role in omega-3 production, fish oil is still a substantial threat to this developing technology because of its low production costs (Martek Annual Report, 2004). Additionally, several companies have developed micro-encapsulated fish oil products that claim to have resolved much of the odor, stability and taste issues associated with fish oil while simultaneously removing the need for costly purification. As a result, decreasing the production cost of the algae culture process remains an indispensable work for the DHA heterotrophic algae producer, and the present invention provides a practical way to do so by using the crude glycerol as an inexpensive carbon source.

Figure 3:
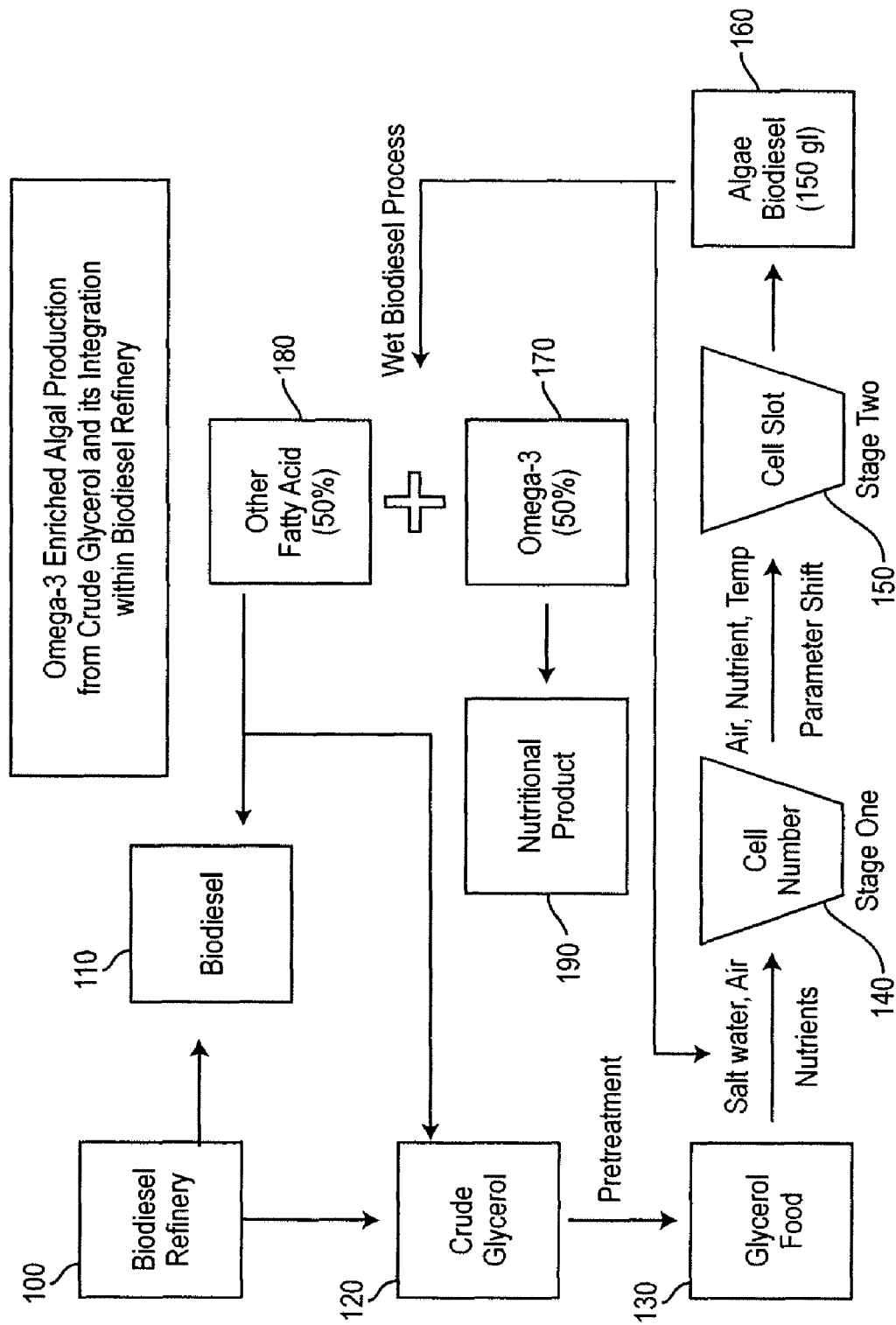
FIG. 3. Schematic representation of the integrated algae-biofuel system.

The integrated microalgae-biodiesel system of the invention is schematically illustrated in FIG. 3. As can be seen, a biodiesel refinery 100 produces biodiesel 110 and crude glycerol 120 as a byproduct. Pretreatment of the crude glycerol 120 yields glycerol feedstock 130. Pretreatment involves pH and fatty acid control through addition of acids. An acid such as hydrochloric acid is added to the crude glycerol with agitation or other mixing method. When the pH decreases to 7.0, especially lower than 4.0, the fatty acid ions convert to free fatty acids and form a layer on the top of the glycerol phase when agitation is stopped. This free fatty acid layer can then be removed by separation of these two different liquid phases. Other impurities such as salts remain in the glycerol. The residual salts are not harmful to the algae, and may serve as algal nutrients for growth. Further, as biodiesel producers refine the production process, the crude glycerol byproduct will likely contain fewer impurities, simplifying the pretreatment procedure. When glycerol feedstock 130 is fed to algae, together with other nutrients, under the initial stage one conditions, the result is an increase in cell number 140. Further processing of the algae under stage-two conditions results in an increase in cell size 150 and the accumulation of lipids. Stage three is a short polishing step whereby the conditions of vessel two are shifted to allow for production of more lipids with an improved PUFA profile. The final biomass 160 that is produced is then processed to yield omega-3 methyl esters 170, which are utilized in nutraceuticals and other products (190). Other methyl esters 180 that are derived from the algae biomass are rechanneled back into biodiesel 110 production. The additional crude glycerol and nutrients produced from biodiesel production 110 can be rechanneled back into the algal fermentation process or, in the case of nutrients, sold as an animal feed, and so on.

In the practice of the invention, any suitable microalgae may be used to produce omega-3 rich lipids. Generally, *Thraustochytrids*, and specifically microalgae of the genera *Thraustochytrium* and *Schizochytrium* will be utilized. In a preferred embodiment, the microalgae used in the fermentation process are *Schizochytrium limacinum* SR 21, a known high-cell density species with unique abilities for efficient metabolism of glycerol carbon sources. By selecting a known glycerol-utilizing strain, the process becomes particularly efficient in regard to both algal production and crude glycerol remediation.

While this three-stage culture process is described herein as used in the production of products using crude glycerol as the feedstock, the method is more widely applicable. The method can be used, for example, for any single cell oil (SCO) producing process, including but not limited to biodiesel production from algae, which is the largest potential SCO application.

The omega-3-rich micro-algae produced by the methods described herein may be used for a variety of purposes. In some instances, the lipid-rich microalgae themselves are used, e.g. as animal feeds, in human foods, in drugs or as nutraceuticals, in cosmetics or in various cleansing agents, or as dietary supplements. Alternatively, the lipids, especially DHA, may be isolated from the microalgae and purified for use in a similar manner. Currently, fish oil is a main ingredient in finfish and marine shrimp feeds, mainly because it offers a range of fatty acid classes, including omega-3, which contribute to the energy, growth, and reproductive demands of the fish. However, the level of PUFA in fish oil varies depending on species, extraction procedure and storage conditions. In fact, standard available fish oils do not offer sufficient levels of DHA ratios to completely satisfy the nutritional demands for reproduction and larval growth (Harel et al., 1994). Consequently, marine oils where the DHA levels are particularly high due to its origin from specific fish tissues, or through special extraction procedures, have been recommended in broodstock diets and larval rearing enrichment preparations, but the availability of these high DHA-containing oils is limited and often prohibitively expensive to produce and the idea of catching fish to feed fish is not especially environmentally friendly. So, the aquaculture industry is now actively investigating alternative nutrient sources, with land-based vegetable and unicellular organisms such as microalgae, yeast, molds, bacteria, and fungi being taken into consideration (Harel et al., 2002).

A major advantage in the use of unicellular organisms as described herein is that they can be easily produced in industrial quantities under controlled and environmentally safe conditions and studies have shown that heterotrophic algal and fungal supplemented diets are highly effective in delivering essential fatty acids either through larval live food enrichment or directly through the fish diet (Harel et al., 2002). Unlike fish oil, which contains various omega-3 and other polyunsaturated fatty acids (PUFA) depending on species, extraction procedure and storage conditions, the dried heterotrophic algae and yeast usually have a very stable rate of PUFA. Furthermore, DHA can be produced by different groups of algae strains separately, and combinations of these alga strains can offer a broader range of fatty acids to meet more effectively the species-specific dietary requirements, which is not realizable with fish oil (Harel et al., 2002).

Another potential use of heterotrophic algal preparations is that they could be very useful in hatcheries of marine finfish, shrimp and various mollusks (claims, oysters, mussles, etc.) to partially substitute or supplement a live algae diet of the larvae, which is very costly when photosynthetic algae are used.

The present invention will also improve the development of an "organic fish" industry, in that it will provide an inexpensive source of omega-3 that does not originate from fish meal. In fact, Omega-3, although widely used in the pharmaceutical, nutraceutical, and food industries, owes its biggest market share to aquaculture fish feed. At present, fish oil production amounts to about 1 million tons annually, of which 70-80% is utilized for the production of fish feed for farmed fish. Currently, farm-raised fish obtain omega-3 only from fish meal. As the aquaculture feed demand increases and ocean fishery resources decline, using fish meal to support aquaculture growth becomes non-sustainable. In addition, the development of an organic fish movement requires an omega-3 source that does not originated from fish meal. Therefore, feeding an organic diet supplemented with enriched omega-3 algae becomes almost the only future option for the aquaculture industry.

DHA enriched biomass and/or extracted oil may also be used as a human food or supplement or nutraceutical. PUFAs can be extracted from microbial sources for use in nutritional and/or pharmaceutical products. For example, DHA-rich microbial oil is manufactured from the dinoflagellate *Crypthecodinium cohnii* and ARA-rich oil is manufactured from the filamentous fungus *Mortierella alpina*, both for use as nutritional supplements and in food products such as infant formula. Similarly, DHA-rich microbial oil from *Schizochytrium* is manufactured for use as a nutritional supplement or food ingredient. Typically, the PUFAs are extracted from biomass and purified although extraction does not necessarily have to occur prior to formulation of the food product. The extracted and purified oils can be further processed to achieve specific formulations for use in food products (such as a dry powder or liquid emulsion).

The PUFA-rich microalgae and/or PUFAs produced by the microalgae may also be used in other applications, including but not limited to cosmetics, cleansers, etc.

EXAMPLES

Example 1

Manipulation of the First Stage Reaction Parameters

Effective manipulation of the first stage reaction parameters as described herein creates a fermentation condition whereby cell number increases exponentially with only a limited diversion of cellular resources to cell growth. This is illustrated in FIGS. 2A-C and Table 2.

Figure 2A:
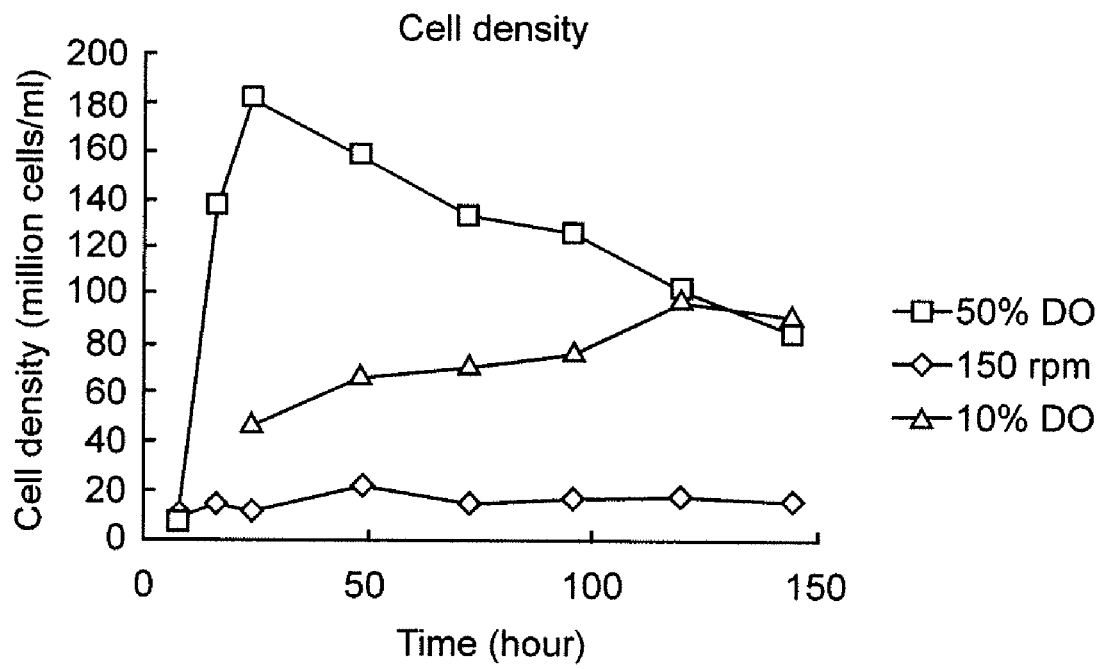
FIGS. 2A-C. Results from cultures with different dissolved oxygen levels: 50%, 10%, and low oxygen control with fixed 150 rpm, in which the dissolve oxygen was less than 5%. A, cell density; B, dry cell weight; C, body weight of each cell.
Figure 2B:
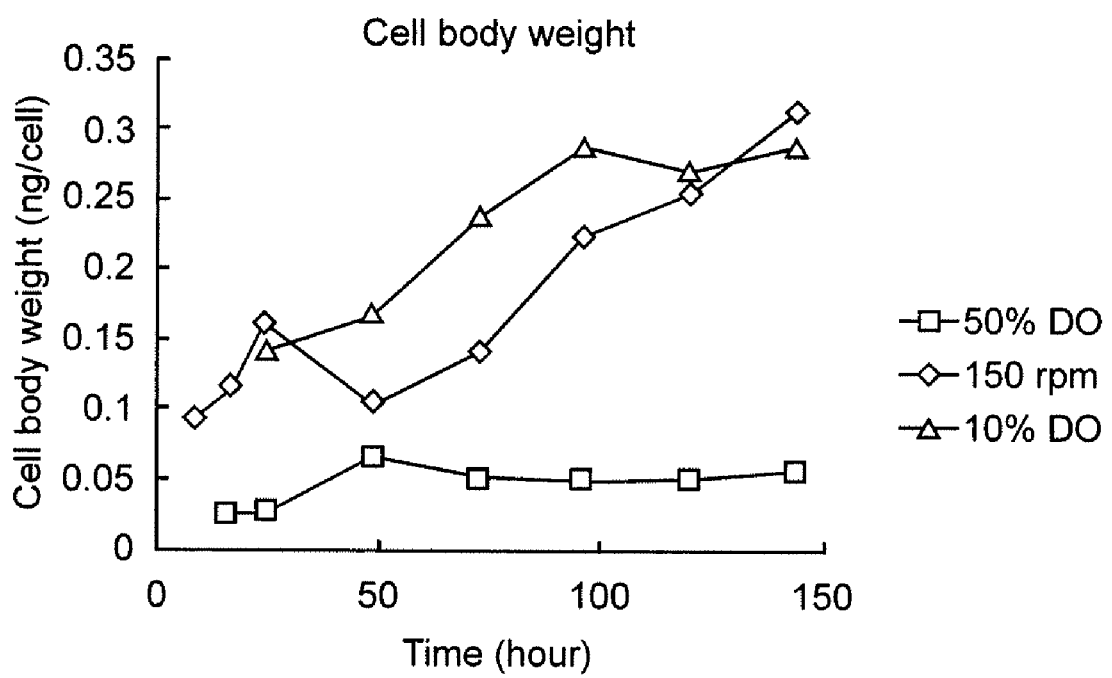
Figure 2C:
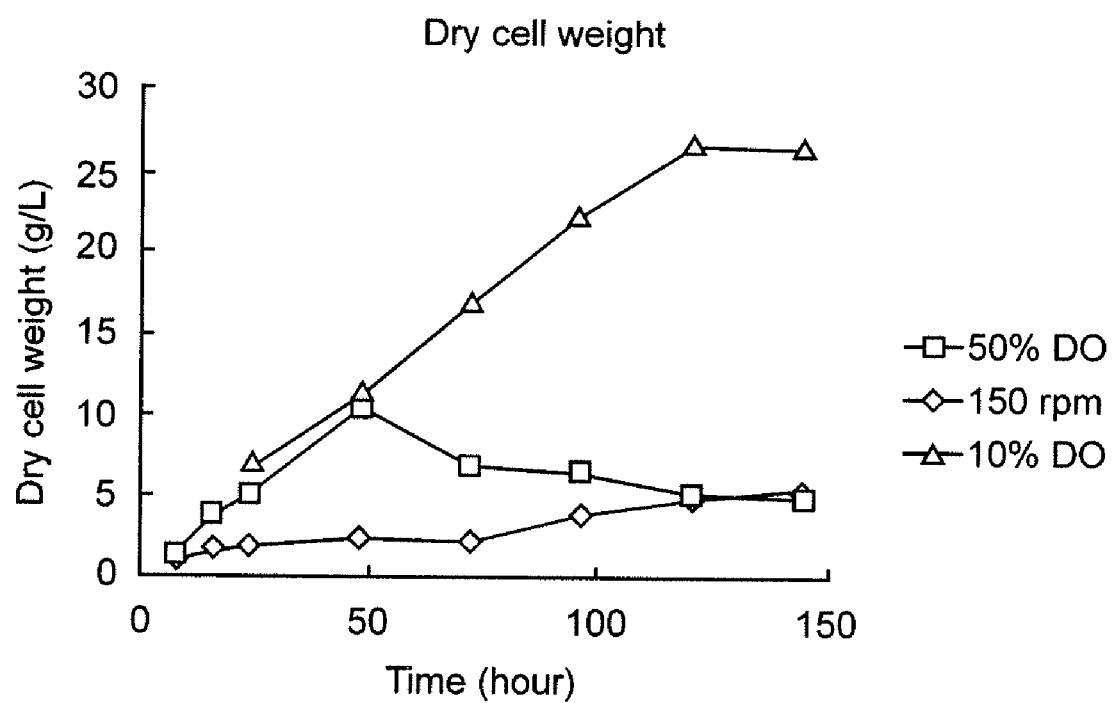

FIGS. 2A-C show that dissolved oxygen (DO) can be a major control (in concert with alterations in temperature and carbon/nitrogen feeds) in the process. As can be seen, by elevating the DO levels, a process was induced whereby cellular energy and resources were devoted to production of chemicals necessary for cell division, thus allowing for a reaction set-up that greatly increases cell number with little effect on cell size. Conversely, a shift towards lower DO does the opposite, producing an environment in which cellular energy and resources are focused on cellular growth and lipid accumulation.

The culture controlled 50% DO produced 181 million cells/ml after 24 hours, but dropped to only 22.5 million cells/ml after 48 hours. The culture with 10% DO produced a cell density about ½ of that at 50% DO, or about 98.4 million cells/ml during the first 24 hours. It is interesting that high DO (50%) control throughout the whole process did not produce a high biomass concentration. The cell density and biomass concentration started to decrease after 24 hours. The final cell body weight was only 0.057 ng/cell, with a high of 0.066 ng/cell at the 48th hour. This clearly showed that high DO control is favorable for the cell's reproduction, but harmful to lipid accumulation. The pH in the later phase of the high DO culture was close to 3.0, which was probably caused by accumulation of organic acids. The culture with 10% DO control produced a cell growth profile similar to cultures with flask, with a final dry cell weigh of 26.5 g/L, and a final cell body weight of 0.290 ng/cell. Although the culture with low DO produced a cell density of only 22.5 million cells/ml, even lower than that in flasks, its biomass concentration kept increasing, producing 5.2 g/L biomass in 6 days, with the final cell body weight of 0.315 ng/cell. Further culture would likely further improve this production. This experiment showed that lower DO results in lower cell density, but is favorable for lipid accumulation.

This was further proved by flask culture of cells that were taken from a control fermentor run at high DO (50%) for 72 hours. After 72 hours of high DO culture in a fermentor, 50 mL of broth was taken from the fermentor and put into a shaker flask, which is assumed to have a low DO concentration, to be cultured further. After continued culture in the flask, the final biomass concentration attained was only a relatively low 20.6 g/L.

It is notable that the culture with 10% DO control produced a much lower cell density than that with 50% DO. U.S. Pat. No. 6,607,900 states that the level of dissolved oxygen present in the fermentation medium is at least about 4% of saturation. Obviously, this is not enough for high cell density culture, since even 10% DO is insufficient. Maintaining DO at this low level produces too few cells, which leads to a low biomass concentration in both the cell size growing and lipid accumulation stages.

In summary, we have shown that (1) high DO leads to cell growth while low DO is needed for lipid or biomass growth; and (2) if the first 24 hours of incubation is carried out at 10% DO (similar to the prior art teaching of 4-8% DO), instead of the preferred 50% DO, cell number increase is not optimal, which will ultimately result in a lower biomass/lipid yield because of the maximal size the cells can achieve. More glycerol (waste carbon) is utilized and more lipid is produced when higher cell numbers are achieved, but this is only possible if the maximal number of cells is produced early in the algal growth process, e.g. in the first 24 hours.

Table 2 illustrates the outcome of such a theoretical, focused process. In the experiment from which the data was obtained, a control which produced lower levels of cell numbers (58.5) ultimately led to a lower value of cell weight (24.6 which is 10% lower) than did a treatment which used the same conditions as the control, except that the cell number was doubled by mixing the cells from two flasks into one and keeping the same nutrient, broth and oxygen amounts. The doubling of cells at a point in the experiment then led in the end to a higher cell number (114.7) and a 10.5% higher cell weight (30.8). Of note, the cell body weight of the control was 0.42 while that of the experimental cells was 0.268. Without being bound by theory, it is likely that, since all parameters other than cell number were the same (e.g. levels of carbon and nitrogen were equivalent) there simply were not enough nutrients available to maximize cell size in the experimental culture. It is likely that, if additional carbon/nitrogen had been supplied, then in the end the cell body weight would have been maximized in the experimental culture, as was the case for the control, and the overall yield would have been enhanced significantly beyond the 10.4% that was observed. Note also that these results are independent of time. Thus, it is likely that if optimal levels of carbon and nitrogen are fed, then all cells will increase in size simultaneously and extra time will not be required to maximize cell size.

TABLE 2

Manipulation of the first stage reaction parameters

| | | Control (no condensing) | Condensing time 24 hrs | Condensing time 48 hrs | Condensing time 72 hrs |
|---|---|---|---|---|---|
| Cell number ($10^6$ cells/ml) | condensed | | 50.4 ± 3.8 | 85.1 ± 8.4 | 94.7 ± 23.8 |
| | final | 58.5 ± 7.7 | 84.1 ± 17.5 | 104.7 ± 9.1 | 114.7 ± 15.9 |
| | difference | | 33.7 | 19.6 | 20.0 |
| Dry cell weight (g/L) | condensed | | 6.9 ± 0.2 | 13.7 ± 0.4 | 20.3 ± 1.2 |
| | final | 24.6 ± 1.6 | 26.2 ± 0.9 | 27.1 ± 0.6 | 30.8 ± 0.9 |
| | difference | | 19.3 | 13.4 | 10.5 |
| Cell body weight (ng/cell) | condensed | | 0.137 | 0.161 | 0.214 |
| | final | 0.420 | 0.311 | 0.259 | 0.268 |
| | difference | | 0.173 | 0.099 | 0.056 |

Example 2

The initial culture medium consists of 40 g/L glycerol, 5 g/L yeast extract and 5 g/L ammonium acetate as the nitrogen source, and other insignificant factors in the salt-water broth. 10% (v/v) of the seed cells from a smaller culture vessel is inoculated to the fermentor. The temperature is controlled at 30° C., and the dissolved oxygen (DO) is controlled at 20%~50%. The first stage, or cell number increasing stage, lasts for about 24 hours, in which the cell number increases very quickly with the final cell density being 400~800 million cells/ml, with the higher the better. When the cell number has stopped increasing, the second stage begins, in which fatty acids are accumulated. The DO is controlled at 3~5% during this stage with the glycerol and nitrogen concentration controlled at 30~50 g/L and 0.5~1.0 g/L by feeding, respectively. The temperature in this stage is still at 30° C., and this stage will last until the 60~80th hour of the whole process until the dry cell weight has stopped increasing. Then, nitrogen feeding will be stopped while glycerol is still fed and controlled at 30 g/L. In this final time period the temperature will be decreased to 20~25 C., and DO will be controlled at about 0.5%, to further accumulate fatty acids and provide for an improved PUFA profile. After about 24~40 hours in this last section the dry cell weight will start to decrease and the whole process is finished and the cells are harvested.

For the first stage, higher temperature and DO is preferred because cells grow much faster at 30° C. than 25° C. (data not shown) and oxygen consumption is very high during cell reproduction. Thus, keeping the temperature and DO high in the first stage is the key to obtaining high cell density. As the cell number stops increasing, the cell size will be increased due to fatty acid accumulation. In this stage, lower DO is preferred because high DO in this stage will harm fatty acid synthesis, and convert the carbon source to other products. The nitrogen concentration in this stage should be kept below 1.0 g/L, and experiment data show that nitrogen concentration higher than this was harmful to the cell growth. In fact, nitrogen limitation is very important for the fatty acids accumulation in nature. However, a certain concentration is demanded in this period, to keep normal metabolism of the cell, for growth of the cell structure, and the enzyme synthesis. At the end of this period, the DHA content in the biomass is about 13~17%, which can be further increased by decreasing the temperature and DO. At the end of the whole process, the nitrogen will be depleted, and low temperature and even low DO further enhance the DHA content to about 20% of the dry biomass. The following shifts (Table 3) in operating parameters are completed between the three different stages. The entire fermentation process then is controlled at about 5 days.

TABLE 3

Shifting of Parameters in Three-Stage Process

| | Hours | | |
|---|---|---|---|
| | 0~24 | 24~80 | 80~120 |
| DO | 50~20% | 5~3% | 0.5% |
| Temperature | 30 | 30 | 20 |
| Glycerol concentration (g/L) | 30~50 | 30~50 | 30 |
| Nitrogen concentration (g/L) | 1.5~1.0 | 1.0~0.5 | 0.5~0 |

Table 4 below delineates the production capabilities of a typical 5-day three-stage fermentation process using the above described shifting protocol, pre-treated crude glycerol and a 5-L fermentor. The final biomass concentration was 137 g/L, and on average the overall conversion rate was 46.2% with an average biomass productivity of 1.14 g/L/hr. However, it is the belief of the investigators that this phase I result can be improved upon with additional optimization. The reason for this belief is that in certain experimental trials at 5-L size, much higher cell number counts (800 million cells/ml) as well as higher final average cell body weights (500 pg/cell) were attained but were difficult to maintain due to concerns regarding consistent feed supply and aeration. It is believed that the present three-stage approach focusing on separating and optimizing the cell number and cell mass stages is capable of achieving yields and productivities that are in line or near the existing commercial processes and potentially could rival existing processes if the feed, mixing and aeration can be further controlled and optimized with continued study.

TABLE 4

Typical Yields and Productivity in Three-Stage Fermentation

| | Hours | | | | | | | | | | |
|---|---|---|---|---|---|---|---|---|---|---|---|
| | 12 | 16 | 24 | 37 | 47 | 57 | 70 | 81 | 95 | 106 | 120 |
| Cell number (million cells/ml) | 212 | 288 | 683 | | | 582 | | | | | 455 |
| Dry cell weight (g/L) | 7.4 | 13.0 | 26.8 | 55.1 | 70.4 | 81.6 | 102 | 126 | 145 | 143 | 137 |
| Cell body weight (pg) | | 45 | 40 | | | 140 | | | | | 301 |
| DCW productivity (g/L/hr) | | 1.40 | 2.15 | 1.94 | 1.53 | 0.76 | 1.57 | 2.18 | 1.37 | | |
| Glycerol consumption rate (g/L/hr) | | | 3.53 | 4.46 | 4.42 | 4.61 | 2.29 | 3.69 | 1.77 | 1.39 | 1.82 |
| Conversion rate (%) | | | 60.9 | 43.5 | 34.6 | 16.5 | 68.6 | 59.1 | 77.6 | | |

The dry biomass obtained from the fermentor reactions were analyzed for important parameters so that a better understanding could be obtained in regard to the success of the fermentation in terms of fats produced, DHA produced, and other important potential aquaculture feed components like protein and amino acid profile. Tables 5-7 summarize the analytical findings of one set of algae produced in the scaled-fermentation experiments. The algae tested was from a 30-L trial. Typically, the fat content in algae biomass tested from smaller 1 and 5-L reactors was more than 50% (data not shown). The fatty acid and amino acid profiles are similar to those of *Schizochytrium* biomass that is commercially available at, for example, the web site located at www.aquafauna.com.

TABLE 5

Analysis of Algae Biomass Produced from Crude Glycerol

| Parameter | % Mass |
|---|---|
| Fat | 34.41 |
| Protein | 37.93 |
| Crude Fiber | 1.80 |
| Ash | 8.51 |
| Carbohydrates | 19.19 |
| Calcium | 0.45 |
| P | 1.92 |
| K | 1.38 |
| Carotenes | 835 IU A/lb |

TABLE 6

Fatty Acid Profile of the Algae Biomass Produced with Crude Glycerol

| Parameter | % MASS | % of Fat |
|---|---|---|
| Moisture (88.9%) | | |
| Saturated Fatty Acids | 15.23 | 44.241 |
| Monounsaturated Fatty Acids | 0.36 | 1.047 |
| Trans Fatty Acids | 0.36 | 1.047 |
| Polyunsaturated Fatty Acids | 16.94 | 49.215 |
| Total Fat | 34.41 | 100.000 |
| C14:0 Myristic | 0.73 | 2.110 |
| C15:0 Pentadecanoic | 0.56 | 1.640 |
| C16:0 Palmitic | 13.77 | 40.000 |
| C17:0 Margaroleic | 0.24 | 0.710 |
| C18:0 Stearic | 0.55 | 1.610 |
| C18:1n9C Oleic | 0.27 | 0.780 |
| C18:2n6 Linoleic | 0.10 | 0.280 |
| C20:0 Arachidic | 0.07 | 0.190 |
| C18:3n3 Linolenic | 0.04 | 0.130 |
| C18:4n3 Octadecatetraenoic | 0.05 | 0.140 |
| C20:3n6 Homo-Gamma-Linolenic | 0.07 | 0.190 |
| C22:1n9 Erucic | 0.07 | 0.190 |
| C20:4n6 Arachidonic | 0.07 | 0.200 |
| C20:4n3 Eicosatetraenoic | 0.17 | 0.480 |
| C20:5n3 Eicosapentaenoic | 0.31 | 0.900 |
| C24:1n9 Nervonic | 0.06 | 0.160 |
| C22:5n6 Docosapentaenoic | 3.89 | 11.300 |
| C22:5n3 Docosapentaenoic | 0.21 | 0.600 |
| C22:6n3 Docosahexaenoic | 12.60 | 36.600 |
| Others | 0.44 | 1.270 |

TABLE 7

Amino Acid Profile of the Algae Biomass Produced with Crude Glycerol

| Parameter | % Mass | % Total Amino Acids |
|---|---|---|
| Protein | 37.93 | |
| Aspartic Acid | 2.52 | 8.946 |
| Threonine | 1.35 | 4.792 |
| Serine | 1.44 | 5.112 |
| Glutamic Acid | 4.50 | 15.974 |
| Proline | 1.26 | 4.473 |
| Glycine | 1.35 | 4.792 |
| Alanine | 2.25 | 7.987 |
| Valine | 2.07 | 7.348 |
| Methionine | 0.63 | 2.236 |
| Isoleucine | 1.17 | 4.153 |
| Leucine | 2.16 | 7.668 |
| Tyrosine | 1.08 | 3.834 |
| Phenylalanine | 1.17 | 4.153 |
| Histidine | 0.54 | 1.917 |
| Lysine | 1.71 | 6.070 |
| Arginine | 1.98 | 7.029 |
| Cysteine | 0.54 | 1.917 |
| Tryptophan | 0.45 | 1.597 |

Example 3

Energy Cost Comparison

Matlab-Simulink software was used to develop an energy cost comparison of the system. Simulation was for a 5-ton fermentor algae process with evaluation based on test data made available from earlier 5 and 30-L experiments.

Basic assumed parameters for the culture were: 5 cubic meter effective fermentor volume; fed-batch feeding protocol; reaction temperature of 30° C.; average environmental temperature of 25° C.; aeration rate of 0.5 vvm and 1.0 vvm and an electricity cost of $0.046/kwh. Basic assumed parameters for the heating system were: heat loss being equal to where q is the heat loss, h is the thermal conductivity of the steel, A is the inside area, Ti is the real inside temperature, and T is the outside temperature; heat required is equal to where Q is the heat required, M is the total mass of solution, Cp is the heat capacity, T is the target inside temperature, and Ti is the real inside temperature. Additional assumed parameters for the heating system were M=5,000 kg; Cp=3.95 kJ/kgK; Thickness of steel=0.005 m; Thickness of insulation=0.02 m; Thermal conductivity of steel=45 W/mK; Thermal conductivity of insulation=0.4 W/mK; and Surface Area=55 m². Basic assumed parameters for the agitation system include an assumed six-blade turbine with disk with a Tank diameter of 3.48 m; Turbine diameter of 1.16 m; Tank height of 5.00 m; Blade width of 0.30 m; Solution density of 1,000 kg/m³; Solution viscosity of 100 cp; and Agitation rate of 300-1,000 rpm. Basic assumed parameters for the aeration system were for the 1 vvm system a piston-type air compressor with 170 cfm; theoretical power input of 50 kw; an efficiency of 0.7 and a Max PSIG of 450. The 0.5 vvm system had only 100 cfm and 27 kw along with 0.7 efficiency and a 450 Max PSIG.

The simulation output as based upon the above parameter assumptions is summarized in Table 8. As can be seen about 52 cents/kg algae are needed for aeration. This combined with the raw material cost estimates as summarized in Table 9 produce a total aeration and feed input cost of about $1 to produce 1 kg of algae biomass. Although this is only a rough estimation, and other factors may increase the total cost there appears to be a positive margin for this production if this algae biomass can be sold wholesale at $10/kg (>50% reduction in retail price).

TABLE 8

Simulation Output for Energy Consumption in Fermentation Process

| | | |
|---|---|---|
| Aeration rate (VVM) | 1 | 0.5 |
| Fermentor size (m³) | 5 | 5 |
| Agitation (rpm) | 800 | 800 |
| Reaction temp. (° C.) | 35 | 35 |
| Reaction time (hr) | 96 | 96 |
| Algae biomass (kg, dry weight) | 860 | 860 |
| Total energy cost ($) | 450 | 350 |
| Energy consumption (dollar/kg Algae) | 0.52 | 0.41 |

TABLE 9

Estimation of Raw Material Cost

| | |
|---|---|
| Conversion rate | 46% |
| Glycerol (kg) | 2.2 |
| Price ($/kg) | 0.12 |
| Glycerol cost ($) | 0.26 |
| Nitrogen and other salts ($) (suppose it equal to the carbon source cost) | 0.26 |
| Total raw material cost (dollar/kg algae) | 0.52 |

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

REFERENCES

Barclay, W. R. "Biomass containing Thraustochytriales microflora," Official Gazette of the United States Patent and Trademark Office Patents (1270:3), 2003.

Belarbi, E. H., Molina, E. and Chisti, Y. "A process for high yield and scaleable recovery of high purity eicosapentaenoic acid esters from microalgae and fish oil," Process Biochemistry (35:9), 2000, pp. 951-969.

Gonzalez-Pajuelo M, Meynial-Salles I, Mendes F, Soucaille P, Vasconcelos I. Microbial conversion of glycerol to 1,3-propanediol: Physiological comparison of a natural producer, *Clostridium butyricum* VPI 3266, and an engineered strain, *Clostridium acetobutylicum* DG1(pSPD5). Appl Environ Micro 2006; 72:96-101.

Harel, M., Koven, W., Lein, I., Bar, Y., Behrens, P., Stubblefield, J., Zohar, Y. and Place, A. R. "Advanced DHA, EPA and ArA enrichment materials for marine aquaculture using single cell heterotrophs," Aquaculture (213:1-4), 2002, pp. 347-362.

Harel, M., Tandler, A., Kissil, G. W. and Applebaum, S. W. "The Kinetics Of Nutrient Incorporation Into Body-Tissues Of Gilthead Seabream (Sparus-Aurata) Females And The Subsequent Effects On Egg Composition And Egg Quality," British Journal Of Nutrition (72:1), 1994, pp. 45-58.

Meesters P, Huijberts G N M, Eggink G. High cell density cultivation of the lipid accumulating yeast *Cryptococcus curvatus* using glycerol as a carbon source. Appl Micro Biotech 1996; 45:575-579.

Narayan M S, Manoj G P, Vatchravelu K, Bhagyalakshmi N, Mahadevaswamy M. Utilization of glycerol as carbon source on the growth, pigment and lipid production in *Spirulina platensis*. Inter J Food Sci Nutri 2005; 56:521-528.

Papanikolaou, S. and Aggelis, G. Lipid production by *Yarrowia lipolytica* growing on industrial glycerol in a single-stage continuous culture, Bioresource Technology (82:1), 2002, pp. 43-49.

Ward O P and Singh A. Omega-3/6 fatty acids: Alternative sources of production. Process Biochem 2005; 40:3627-3652.

Yokochi T, Honda D, Higashihara T, Nakahara T. (1998). Optimization of docosahexaenoic acid production by SR 21. Applied Microbiology and Biotechnology. 49: 72-76.

We claim:

1. A method for producing fatty acids, comprising the steps of
   i) culturing microalgae under 20-50% dissolved oxygen (DO) from 1-24 hours to promote high cell density via cell proliferation which increases cell number; then
   ii) culturing said microalgae under 3-5% DO from 24-80 hours to promote an increase in cell size and accumulation of fatty acids, during which step microalgae cells decrease or cease proliferation; and then
   iii) culturing said microalgae under 0.5% DO from 80-120 hours to promote accumulation of fatty acids;
   wherein said conditions of each of culturing steps i), ii) and iii) are different from one another.

2. The method of claim 1, wherein said fatty acids are enriched for omega 3 polyunsaturated fatty acids.

3. The method of claim 1, wherein said fatty acids are enriched for docosahexaenoic acid (DHA).

4. The method of claim 1, wherein a primary carbon source for said method is crude glycerol.

5. The method of claim 4, wherein said crude glycerol is pretreated by addition of acids and removal of free fatty acids.

6. The method of claim 4, wherein said crude glycerol is a byproduct of biodiesel production.

7. The method of claim 1, wherein said high cell density is from 400 million to 800 million cells per milliliter of medium.

8. The method of claim 1, wherein said microalgae is from a genus selected from the group consisting of *Thraustochytrium* and *Schizochytrium*.

9. The method of claim 8, wherein said microalgae is *Schizochytrium limacinum* SR21.

10. The method of claim 1, wherein steps i), ii) and iii) are carried out in a single fermentor.

11. The method of claim 1, wherein step i) is carried out in a first fermentor and steps ii) and iii) are carried out in a second fermentor.

12. The method of claim 1, wherein steps i), ii) and iii) are each carried out in a separate fermentor.

13. The method of claim 1, wherein
   step i) is carried out at 30° C., 30-50 g/l glycerol and 1.0 to 1.5 g/l nitrogen,
   step ii) is carried out at 30° C., 30-50 g/l glycerol and 0.5 to 1.0 g/l nitrogen; and
   step iii) is carried out at 20° C., 30 g/l glycerol and 0 to 0.5 g/l nitrogen.

* * * * *